(12) United States Patent
Saito

(10) Patent No.: US 6,196,997 B1
(45) Date of Patent: Mar. 6, 2001

(54) SYRINGE

(76) Inventor: Yoshikuni Saito, 1930 Doaza Kitanogami, Kurobamemachi, Tochigi, 324-0231 (JP)

( * ) Notice: Subject to any disclaimer, the term of this patent is extended or adjusted under 35 U.S.C. 154(b) by 0 days.

(21) Appl. No.: 09/403,601
(22) PCT Filed: Apr. 24, 1998
(86) PCT No.: PCT/JP98/01908
  § 371 Date: Jan. 31, 2000
  § 102(e) Date: Jan. 31, 2000
(87) PCT Pub. No.: WO98/48871
  PCT Pub. Date: Nov. 5, 1998

(30) Foreign Application Priority Data

Apr. 25, 1997 (JP) .................................................. 9/122976

(51) Int. Cl.⁷ .................................................. A61M 5/00
(52) U.S. Cl. .......................................... 604/110; 604/195
(58) Field of Search .................................... 604/110, 187, 604/218, 228, 195

(56) References Cited

U.S. PATENT DOCUMENTS 5,716,341   2/1998   Saito .

FOREIGN PATENT DOCUMENTS 0 633 036   1/1995   (EP) .
3-97468     4/1991   (JP) .
7-31681     2/1995   (JP) .
8-141082    6/1996   (JP) .
WO96/15820  5/1996   (WO) .

Primary Examiner—John D. Yasko
(74) Attorney, Agent, or Firm—Eckert Seamans Cherin & Mellott, LLC

(57) ABSTRACT

A disposable syringe mainly used in medical treatment facility and formed so that the piston (4) is pulled into the inside of the syringe body (21) with the needle support (6) by pulling out the piston (4) after the locking projection (9) of the piston *tip is inserted into and engaged with the locking hole (70) of the needle support (6) by pressing in the piston (4). The locking structure for preventing the needle support (6) from slipping off in one end direction of the syringe body (21) is provided between the inner peripheral face of the smaller-diameter portion (23) and the outer peripheral face of the needle support (6) and the seal structure for preventing liquid leak is formed in the locking portion of the locking structure (100) and, when the locking projection (9) is inserted into and engaged with the locking hole, the needle support (6) is deformed to expand the inner peripheral face of the smaller-diameter portion (23) in the radial direction and disengage the engagement of the locking structure (100). With the sealability of the seal structure (110) kept in high level, drawing out (removing) of the needle support (6) is made smooth owing to the expansion of the smaller-diameter portion (23).

14 Claims, 8 Drawing Sheets

SYRINGE

BACKGROUND OF THE INVENTION

1. Field of the Invention

The present invention relates to a disposable syringe mainly used in medical treatment.

2. Description of the Prior Art

A syringe needle of the syringe after use is attached with patient's blood and the like containing pathogenic bacteria etc. When the syringe needle attached with blood or the like is reused, there is a possibility of triggering a secondary infection. To prevent such a secondary infection, a number of disposable syringes are used. As the disposable syringe, for example, like the syringe as disclosed in Japanese Patent Laid-Open No. 31681/1995 (hereinafter referred to as "a conventional syringe"), a syringe (a lead-in type syringe needle) of the system is generally known where the syringe needle attached with blood or the like after use is inserted into a syringe body of the syringe and discarded after kept in a state of being untouchable from outside.

The conventional syringe comprises; a syringe body; a piston sliderably inserted from one end of the syringe body; a smaller-diameter portion formed at the other end in the opposite direction of one end of the syringe body; a needle support detachably supported by the smaller-diameter portion; a syringe needle supported by the needle support; a stopper formed in a tip of the smaller-diameter portion for preventing the needle support from slipping off in the other end direction of the syringe body; an locking projection from a tip of the axis center direction of the piston; and a locking hole disposed on a syringe side of the needle support for engaging with said locking projection when the piston is pressed in, and wherein, after the locking projection is inserted into and engaged with the locking hole by pressing in the piston, the syringe needle with the needle support is pulled into the syringe and stored there by pulling out the piston.

the conventional syringe is widely used even today in medical field and the like. However, the inventor was not satisfied with it and continued to engage in research work by seeking for a method of improving usable facility. What the inventor aimed at is whether removal of the needle support from the syringe body could be made more smoother than before. To make removal of the needle support smooth, a locking structure with the needle support and the syringe body may be made into a structure easy to disengage. This is because, if the structure is easy to disengage, a tensile force at the time when the needle support is pulled into the syringe body together the syringe needle may be to be weak.

However, if the structure easy to disengage is adapted, a trouble tends to arise where a sealability between the needle support and the syringe body is lost and parenteral solution leaks out from the syringe body. This is particularly true of a syringe of the system where the syringe needle is used with the needle support is attached. That is, since a compressive force at the time when the syringe needle is attached acts upon this locking structure, the locking structure can not be extremely weak no matter how smooth drawing out should be made. To satisfy at once a conflicting demand for both making drawing out (removal) smooth and sufficiently keeping sealability in high level is the object to be solved of the present invention.

DISCLOSURE OF THE INVENTION

To solve the above mentioned object, the locking structure is required to be such that it works strongly when an injection is executed actually or works weakly or does not work at all when the needle support is drawn out from the syringe body. The inventions as mentioned in respective claims are made from this view and detailed contents thereof will be described again in separate paragraphs to follow.

The 1st invention comprises; a cylindrical syringe body; a piston sliderably inserted (frequently insertable) from one end (an end of the other end) of the syringe body; a smaller-diameter portion having an inside-diameter smaller than an inside-diameter of the syringe body and formed at the other end (an end in the opposite direction of the one end) of the syringe body; a needle support detachably (attachably and detachably) supported by the smaller-diameter portion; a syringe needle supported by the needle support; a pass-through hole formed in the needle support for communicating with the flow passage of the syringe needle and the inside of the syringe body; a stopper formed on a tip portion of the smaller-diameter portion for preventing the needle support for slipping off in the other end direction (in the direction where the syringe needle is available) of the syringe body; a locking projection projected from a tip of an axis center direction of the piston (toward the direction where the needle support is available); and a locking hole disposed on the piston side of the needle support for engaging with the locking projection when the piston is pressed in, and wherein a structure of the syringe is basically the same with the conventional syringe in that the syringe needle, after the locking projection is inserted into and engaged with the locking hole by pressing in the piston, is pulled into the inside of the syringe body and stored there by pulling out the piston. No restriction is imposed on the shape of the needle support. The syringe needle and the needle support may be united or separated. The reason why an inner diameter of the smaller-diameter portion is made smaller than the inner diameter of the syringe body is to make an outer peripheral face of the needle support to be drawn out so as not to contact with an inner peripheral face of the syringe body. That is, if the inner diameter of the syringe body is equal to the inner diameter of the smaller-diameter portion, the outer peripheral face of the needle support has to slide along, that is, has to be drawn out, while contacting with the inner peripheral face of the syringe body. To prevent such a contact, the inner diameter is made smaller.

A structural characteristic of the 1st invention is such that the locking structure for preventing the needle support from slipping off in one end direction of the syringe body is provided between the inner peripheral face of the smaller-diameter portion and the outer peripheral face of the needle support; a seal structure is formed for preventing liquid leak in a locking portion of the locking structure; and the locking projection and the locking hole are formed in the shape where the engagement of the locking structure is disengaged and the needle support is deformed to expand the inner peripheral face of the smaller-diameter portion in the radial direction when the locking projection is inserted into and engaged with the locking hole. The shape of "the locking projection" and "the locking hole" may be of any shape if the engagement of the locking structure can be disengaged through the syringe support.

The 1st invention basically generates the same action effect with the conventional syringe such that after injection the piston is further pressed in and the locking projection is inserted into and engaged with the locking hole and then the piston is drawn out and the needle support can be pulled into the inside of the syringe body with the syringe needle and stored there. A support of the needle support by the smaller-diameter portion is executed by making the needle support pressurized from the syringe body side and climbed over the locking structure. The needle support once supported can not be slipped out of the smaller-diameter portion owing to the stopper and the locking structure. The stopper acts when the piston is pressed in and the locking structure acts when, for example, the syringe needle is attached. The seal structure prevents parenteral solution injected into the syringe body from leaking outside. When the locking projection is inserted into and engaged with the locking hole, the needle support is deformed to expand the inner peripheral face of the smaller-diameter portion in the radial direction, thereby disengaging the engagement of the locking structure. Since the engagement which prevented the needle support from moving in the piston direction is disengaged, drawing out of the needle support can be smoothly executed.

The structural characteristics of the 2nd invention is such that, with limitation imposed on the structure of the 1st invention, the outer diameter of the locking projection before engagement is larger than the inner diameter of the locking hole before engagement.

The 2nd invention generates the action effect such that, with limitation imposed on the action effect of the 1st invention, owing to dimensional difference between the outer diameter of the locking projection and the inner diameter of the locking hole before locking, the needle support is deformed to expand the inner peripheral face of a smaller-diameter cylindrical portion in the radial direction after engagement. Dimensional difference between the outer diameter of the locking projection and the inner diameter of the locking hole expands the locking hole and its expansion is transmitted to the needle support, thereby finally expanding the inner peripheral face of the smaller-diameter cylindrical portion.

The 3rd invention is characterized in that, with limitation imposed on the structure of the 1st or the 2nd invention, a deformation promoting slit (a notch) is formed along with said locking hole in the longitudinal direction of this needle support. The number of slits may be one or more than two.

The 3rd invention generates the action effect such that, in addition to the action effect of the 1st or the 2nd invention, the locking projection is expanded to help deform the needle support when engaged with the locking hole.

The 4th invention is characterized in that, with limitation imposed on the structure of the 3rd invention, the locking projection comprises a communication path for communicating with the inside of the syringe body and the pass-through hole when engaged with the locking hole. The shape of the flow passage may be of any shape provided that the parenteral solution or the air of the like left inside the syringe body can be escaped to the pass-through hole of the needle support when engaged.

The 4th invention is such that, in addition to the action effect of the 3rd invention, the inside of the syringe body communicates with the flow passage of the syringe needle owing to effect of the communication path when the locking projection is engaged with the locking hole (in the case where the locking projection obturates the locking hole). By this manner, the parenteral solution or the air or the like left inside the syringe body can be escaped from the communication path of the locking projection to the pass-through hole of the needle support and then from the pass-through hole to the outside through the flow passage of the syringe needle. That is, no parenteral solution or the like left inside the syringe body owing to press of the piston into the syringe body is confined within the syringe body. By this manner, since pressure which the piston receives from the left-over parenteral solution or the like can be reduced, the engagement of the locking projection with the locking hole can be executed by that much.

The structural characteristics of the 5th invention is such that, with limitation imposed on the structure of either one of the 1st, the 2nd and 4th invention, the locking structure is formed to act a compressive force (pressing force) of the stopper direction (the other end side direction of the syringe body) upon the needle support supported by the smaller-diameter portion and the needle support is formed to undergo elastic deformation owing to the compressive force. By the "elastic deformation", a deformation is meant which is turned back (restored) to is original state when a force is removed from an object deformed by adding the force below elastic limit.

The 5th invention is such that, in addition to the action effect of either one of the 1st, the 2nd and the 4th invention, the locking structure presses the needle support to the stopper, thereby making the needle support undergo the elastic deformation. In the inner part of the inside of the needle support, the compressive stress is generated so that the needle support may turn back to its original state. However, owing to interference from the locking structure, the needle support can not turn back to is original state. Here when the inner peripheral face of the smaller-diameter portion is expanded in the radial direction and by this expansion the locking structure is disengaged, the compressive stress makes the needle support spring out in the drawing out direction (one end direction of the syringe body). That is, since the compressive stress acts so as to help draw out the piston, drawing out is smoothly executed.

The structural characteristics of the 6th invention is such that, with limitation imposed on the structure of the 5th invention, the locking structure includes an annular projection projecting to the center from the inner peripheral face of the smaller-diameter portion and the annular protrusion protruding in the radial direction from the outer peripheral face of the needle support, and the annular protrusion is located at the other end side of the syringe body from the annular projection. The "annular projection" and the "annular protrusion" are applicable to every possible shapes adaptable by those skilled in the art within the scope of the object of the present invention. The reason why different names of the "annular projection" and the "annular protrusion" are used in the present specification is simply to make both distinguishable and there is no intention to suggest that both should have definitely different shapes. Therefore, there are some cases where a sectional shape of the "annular projection" and the sectional shape of the "annular protrusion" are different from or equal to each other. The reason why an expression: "annular" is used is because projections (protrusions) are formed in the shape of a ring if looked upon from the perpendicular direction toward the axis center, since the projections "the protrusions" are formed across all the area of the inner peripheral face (the outer peripheral face) of the smaller-diameter portion (the needle support).

The 6th invention is such that, with limitation imposed on the action effect of the 5th invention, it generates the action effect as the locking structure, owing to interaction between the annular projection and the annular protrusion. Further, since the projection and the protrusion are formed in the shape of the ring, the whole of the outer peripheral face of the needle support (the inner peripheral face of the smaller-diameter portion) can be thoroughly sealed.

The structural characteristics of the 7th invention is such that, with limitation imposed on the structure of the 6th invention, the annular projection comprises an inclined face inclining downward in one end direction (the piston direction) of the syringe body. To support the needle support by the smaller-diameter portion, the needle support is formed so as to be pressurized from the syringe body side with the annular protrusion climbing over the annular projection and the annular protrusion thus climbed over engaged with the annular projection.

The 7th invention generates the action effect such that, in addition to the action effect of the 6h invention, owing to effect of the inclined face, the annular protrusion is guided and can be easily climbed over. Since the annular projection is easily climbed over, pressurizing the needle support into the smaller-diamter portion can be executed smoothly.

The 8th invention is characterized in that, with limitation imposed on the structure of the 6th or the 7th invention, the annular protrusion is formed in the shape which can bite into the smaller-diamter portion when engaged with the annular projection (including annular protrusion), that is, in the shape expanding the touch area between both. The "shape which can bite into" may be of any shape provided that the annular protrusion can bite into the smaller-diamter portion and such a shape can be realized by forming a diameter directional section of the annular protrusion in the shape of a circular arc or a triangular.

The 8th invention is such that, in addition to the action effect of the 6th or the 7th invention, owing to the annular protrusion biting into the smaller diamter portion, the touch area between both becomes larger with the compressive stress between the smaller-diameter portion and the needle support becoming also larger owing to the bite. By this manner, the sealability between the annular protrusion and the smaller-diamter portion (annular projection) becomes higher.

The 9th invention is characterized in that, with limitation imposed on structure of the 8th invention, either one of the smaller-diameter portion and the needle support is constituted of materials softer than the other. The needle support may be constituted of materials softer than the smaller-diamter portion, or the smaller-diameter portion may be constituted of materials softer than the needle support.

The 9th invention is such that, in addition to the action effect of the 8th invention, it generates the action effect such that the annual projection is deformed when pressurized since either one (for example, the smaller-diameter portion) from among the smaller-diameter portion and the needle support is constituted of soft materials and, therefore, pressurizing is executed smoothly, and particularly in relation to the 8th invention, the bite of the locking portion can be made larger with the sealability between both kept higher by that much.

The structural characteristics of the 10th invention is such that, with limitation imposed on the structure of the 9th invention, the sectional shape of the annular protrusion is in the shape of the circular arc.

The 10th invention generates the action effect such that, in addition to the action effect of the 9th invention, particularly in relation to the 7th invention, the annular projection can be easily climbed over since the touch area with the inclined face can be made smaller, and also in relation to the 8th and the 9th invention, the annular projection easily bites into the needle support and the touch area after biting becomes larger with the sealability kept higher by that much.

BEST MODE FOR CARRING OUT THE INVENTION

Figure 3:
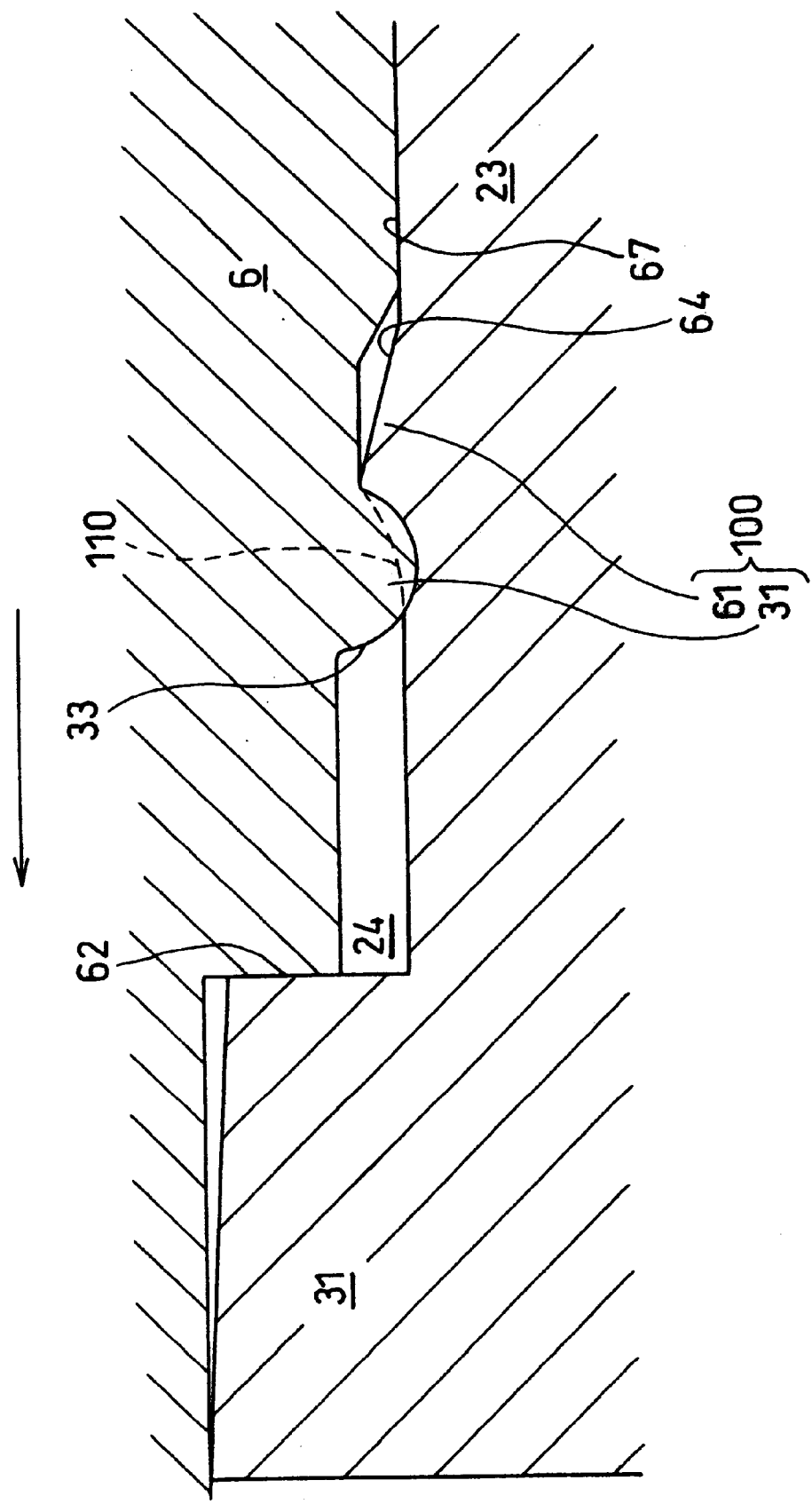
FIG. 3 is an enlarged sectional view of the locking structure as shown in FIG. 2.
Figure 4:
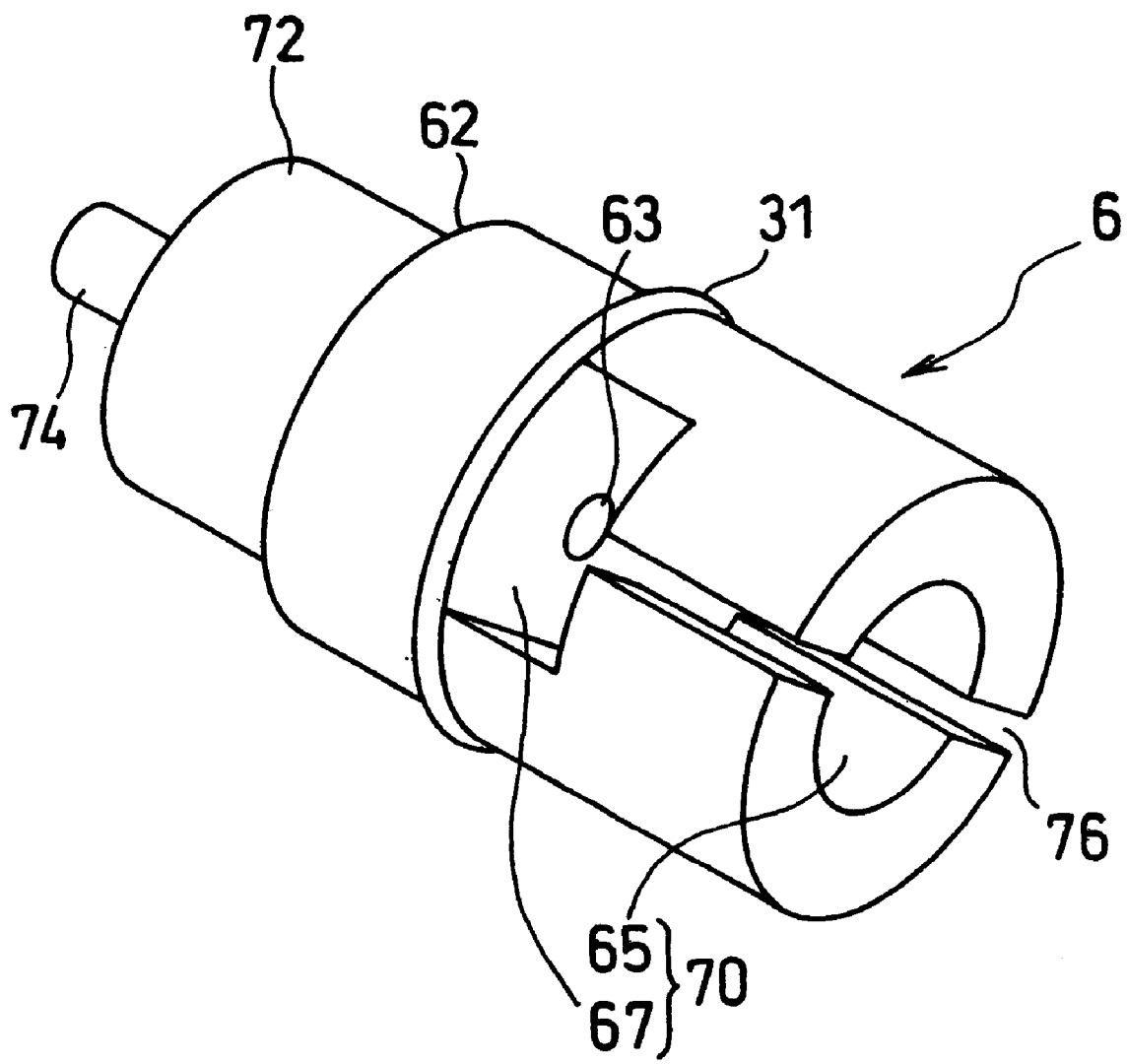
FIG. 4 is a squint-eyed view of the needle support.

The present inventions will be described more in details with reference to the accompanying drawings. Note that each drawing except for FIGS. 3 and 4 shows a piston and a locking projection without being broken for description's sake.

Figure 1:
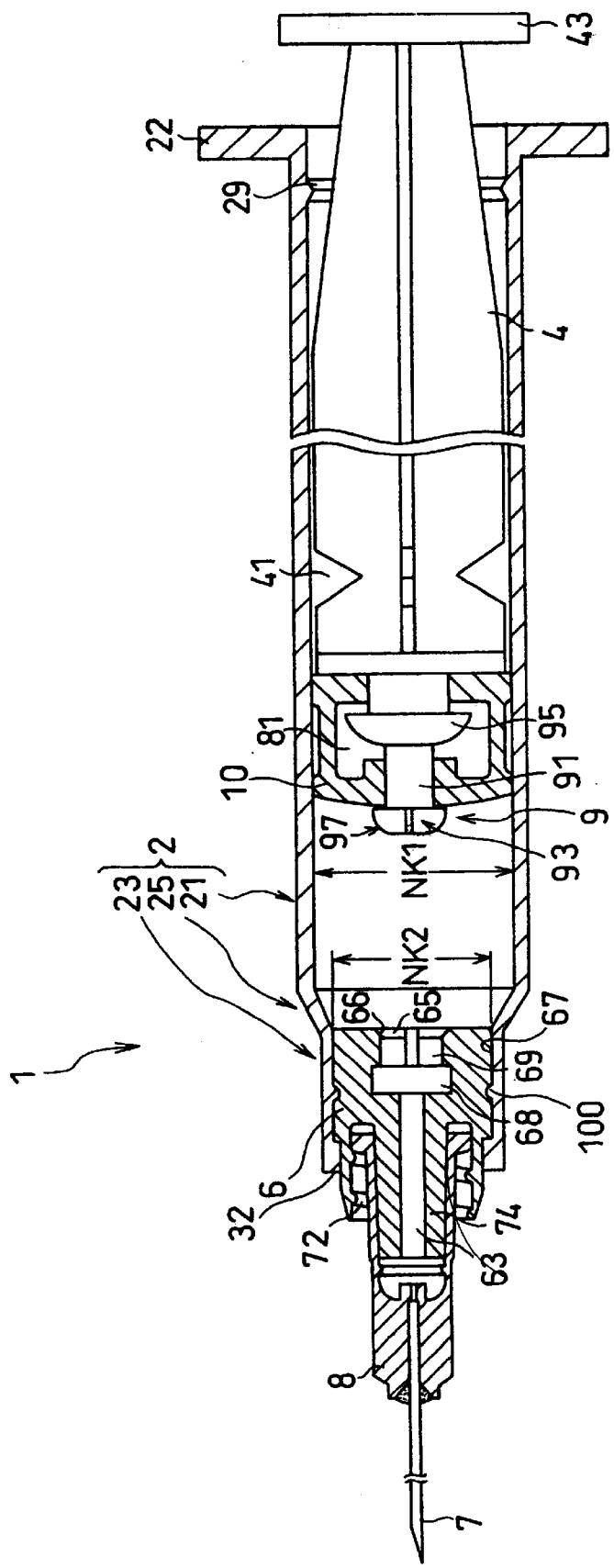
FIG. 1 is a type sectional view, showing one example of the syringe according to the present invention.

A syringe 1 as shown in FIG. 1 comprises; a syringe 2 of resin make; a piston 4 sliderably inserted (frequently insertable) from one end side (right side of FIG. 1) of the syringe 2; and a needle support 6 for a needle mounting attached to the other end side of the syringe 2. A tip of the piston 4 comprises a locking projection 9 unitedly formed and a packing 10 engagedly installed on this locking projection 9. The needle support 6 supports a syringe needle 7 fixed to a hub (a needle base) 8 so as to be detachable.

Figure 2:
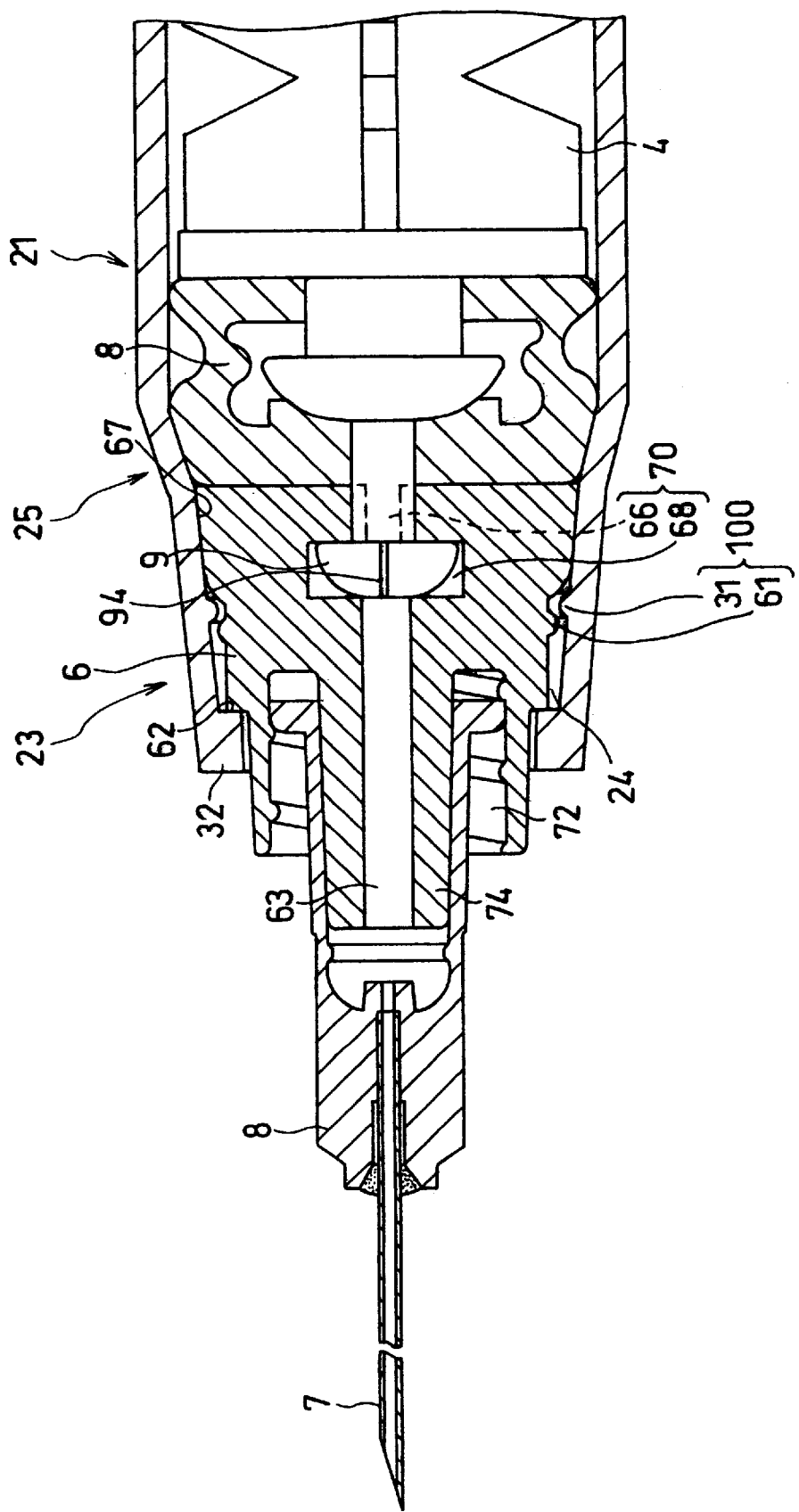
FIG. 2 is an enlarged section view in the vicinity of the smaller-diameter portion of the syringe as shown in FIG. 1.

The syringe 2 comprises a cylindrical syringe 21 having an inner diameter NK1 and a smaller-diamter portion 23 having an inner diamter NK2 smaller than the syringe 21 and comprises a taper portion 25 between the syringe body 21 and the smaller-diameter portion 23. The syringe body 21 comprises a finger support 22 in the shape of a brim at its one end so that fingers can hold it when injections executed. A reference numeral 29 is a locking rib for locking the piston 4 not to slip off from the syringe body 21. The smaller-diameter portion 23 comprises a stopper 32 projecting in the shape of the ring to the central direction so that the needle support 6 may not slip off to the other end direction (a tip direction of the smaller-diameter portion 23) of the syringe body 21. Slipping off of the needle support 6 to the direction of the syringe body 21 is prevented by a locking structure 100 formed between an inner peripheral face of the smaller-diameter portion 23 and an outer peripheral face of the needle support 6. The locking structure 100 of the present embodiment is constituted of an annular projection 31 projection to the center from the inner peripheral face of the smaller-diamter portion 23 and an annular protrusion 61 protruding in the radial direction from the outer peripheral face of the needle support 6. A detailed description of the locking structure 100 will be made again hereinafter. The syringe 2 can be formed by every possible materials adaptable by those skilled in the art if within the scope of the object of the present invention and may be formed by using resin of, for example, polyurethane, poly vinyl chloride, polypropylene, polyethylene and the like. According to experiments conducted by the inventor, hardness of the syringe 2 was most preferable within the scope of, for example, about 40~115 in Rockwell hardness (R scale). As shown in FIGS. 2 and 4, the needle support 6 can be pressurized into the smaller-diameter portions 23 from the syringe body 21 direction and is formed in the shape so as to be drawn out from the syringe body 21 direction after use.

The needle support 6 comprises a stage portion 62 on part of its way and contacts with the stopper 32 of the smaller-diameter portion 23 so as not to slip off when pressurized. The needle support 6 comprises in its center portion a pass-through hole 63 for sending parenteral solution to a syringe needle 7 and this pass-through hole 63 communicates with a locking hole 70 formed in the syringe body 21 side. The locking hole 70 is for engaging with a locking projection 9 of the tip of the piston 4 and disengaging the engagement of a locking structure 100 when drawn out so that the needle support is drawn in and stored inside the syringe body 21. The locking hole 70 is constituted of; and introductory portion 65 comprising a taper face 66 formed in the shape of a fan unfolding toward the locking projection 9 direction; a necking portion 69; and a holder portion 68 having a larger inner diameter than the necking portion 69, and receives the locking projection 9 as described hereinafter to securely hold it.

In FIG. 4, the reference numeral 76 shows a slit for communicating with the holder portion 68 and the inside of the syringe body 21, the reference numeral 72 a screw portion for screwing the hub 8 and, further, the reference numeral 74 a hub mounting portion for mounting the hub 8, respectively. The slit 76 is a slit for making the needle support easily deformed when the locking projection 9 is engaged with the locking hole 70. It is to be noted that the needle support 6 is formed by using materials similar to the syringe 2 and, according to experiments conducted by the inventor, hardness of the needle support 6 was most preferable within the scope of, for example, about 70~150 in R scale for keeping the sealability ad easiness of the disengagement of the locking structure to be described hereinafter. Thus in the present embodiment, the needle support 6 is formed harder than the syringe 2. However, on the contrary, the needle support 6 may be formed softer than the syringe 2.

The needle support 6 is divided into a wider portion and a narrower portion in its outer diameter with the annular protrusion 61 as a boundary. The wider portion has a slightly larger outer diameter than the inner peripheral face of the smaller-diameter portion 23 as shown in FIG. 2 and is designed to form a press portion 67 tightly fitting to this inner peripheral face after pressurized. On the other hand, the narrower portion is designed to form a clearance space 24 between it and the inner peripheral face of the smaller-diameter portion 23 after pressurized. The reason why the press portion 67 and the clearance space 24 are formed will be described hereinafter with description of the action of the present embodiment.

On the basis of FIG. 3, the locking structure 100 will be described. As described above, the locking structure 100 is constituted of the annular protrusion 61 formed in the outer peripheral face of the needle support 6 and the annular projection 31 formed in the inner peripheral face of the smaller-diameter portion 23. Since the locking structure 100 is for preventing the needle support 6 from slipping off toward the syringe body 21, the annular projection 31 is designed to be located in the syringe 21 direction (right side of FIG. 3) from the annular protrusion 61. Further, a longitudinal relative position of the annular protrusion 61 and the annular projection 31 is formed such that, when the annular protrusion 61 is slightly shifted toward the syringe body 21 direction from the annular projection 31 and both engages with each other, the compressive force of the stopper 32 direction acts upon the needle support 6 through the annular protrusion 61. The annular protrusion 61 is in the shape of a circular arc where a sectional shape of the diameter direction comprises a circular arc face 33 and similarly the annular projection 31 is in the shape of a triangle where the sectional shape comprises an inclined face 64. The reason why the sectional shape of the annual protrusion 61 is formed in the shape of a circular arc is because, when the needle support 6 is pressurized into the smaller-diameter portion in the arrow direction, the touch area with the inclined face 64 has to be as little as possible and easy to climb over and also because a seal structure 110 to be described hereinafter has to be easily formed after climbing over.

That is, when the annular protrusion 61 is pressurized into the smaller-diameter portion 23, since the smaller-diameter portion 23 (the syringe 2) is softly formed than the needle support 6 as described above in the present embodiment, combined with the compressive force acting on the stopper 32 direction as described above, the circular arc face 33 bites into the smaller-diameter portion 23 and a strict seal structure 110 (a portion as shown by dotted lines) is designed to be formed. The annular projection 31 and the annular protrusion 61 are not restricted to the shapes as shown in the present embodiment and it is needless to say that, according to an engaging degree of the locking structure 100 and difference of sealing performance of the seal structure 110, other shapes may be adapted. For example, in the case where the needle support is softly formed than the syringe 2 contrary to the present embodiment, the sealability does not have to be harmed advantageously when the shape of the annular projection 31 and the annular protrusion 61 is inversely formed.

Returning to FIG. 1, the piston 4 will be described. The piston 4 is cross-shaped at a section of the perpendicular direction to a paper face and comprises a notch 41 in the shape of a wedge for easily breaking off the piston 4 when thrown away and a press plate 43 for applying the thumb when injections executed. As shown in FIG. 2, the piston 4 comprises the locking projection 9 at its tip and comprises a packing 10 on the midway to the locking projection 9. The packing 10 is formed of resign which is bendable, that is, flexible resin and is sliderable against the inner peripheral face of the syringe body 21 and closes its inside in watertight. The packing 10 comprises a space 81 for deformation promotion in its inside and is easy to deform in the longitudinal direction of the syringe body 21. The packing 10 is engaged with and installed on a support 95 formed on midway to the locking projection 9.

The locking projection 9 comprises a pillar portion 91, the support 95 formed on midway to the pillar portion 91 and an insertion portion 93 formed on the tip portion, and the insertion portion 93 is formed in the shape of a brim comprising a diameter larger than an outer diameter of the pillar portion 91 as shown in FIG. 2. The insertion portion 93 comprises a slit (a communication path) for communication with the inside of the syringe body 21 and the pass-through hole 63 of the needle support 6 when engaged with the locking hole 70. The pillar portion 91 is formed in the length which comes in a position corresponding to the necking portion 69 and the insertion portion 93 in the length which comes in the position corresponding to the holder portion 68, respectively. The insertion portion 93 comprises a taper face 97 taperng off toward the locking hole 70 and is formed so as to cooperate and easily engage with a taper face 66 of the introductory portion 65 when engaged with the locking hole 70. The outer diameter of the insertion portion 93 is formed larger than the inner diameter of the holder portion 68 and the outer diameter of the pillar portion 91 is formed larger than the inner diameter of the necking portion 69, respectively. As a result, when the locking projection 9 is engaged with the locking hole 70, the insertion portion 93 expands (deforms) the holder portion 68 and at the same time the pillar portion 91 expands (deforms) the necking portion 69. Consequently, the needle support 6 is deformed so that the inner peripheral face of the smaller-diameter portion 23 is expanded in the radial direction. For this reason, it is necessary that the locking projection 9 is formed of materials harder than materials forming the needle support 6.

Figure 5:
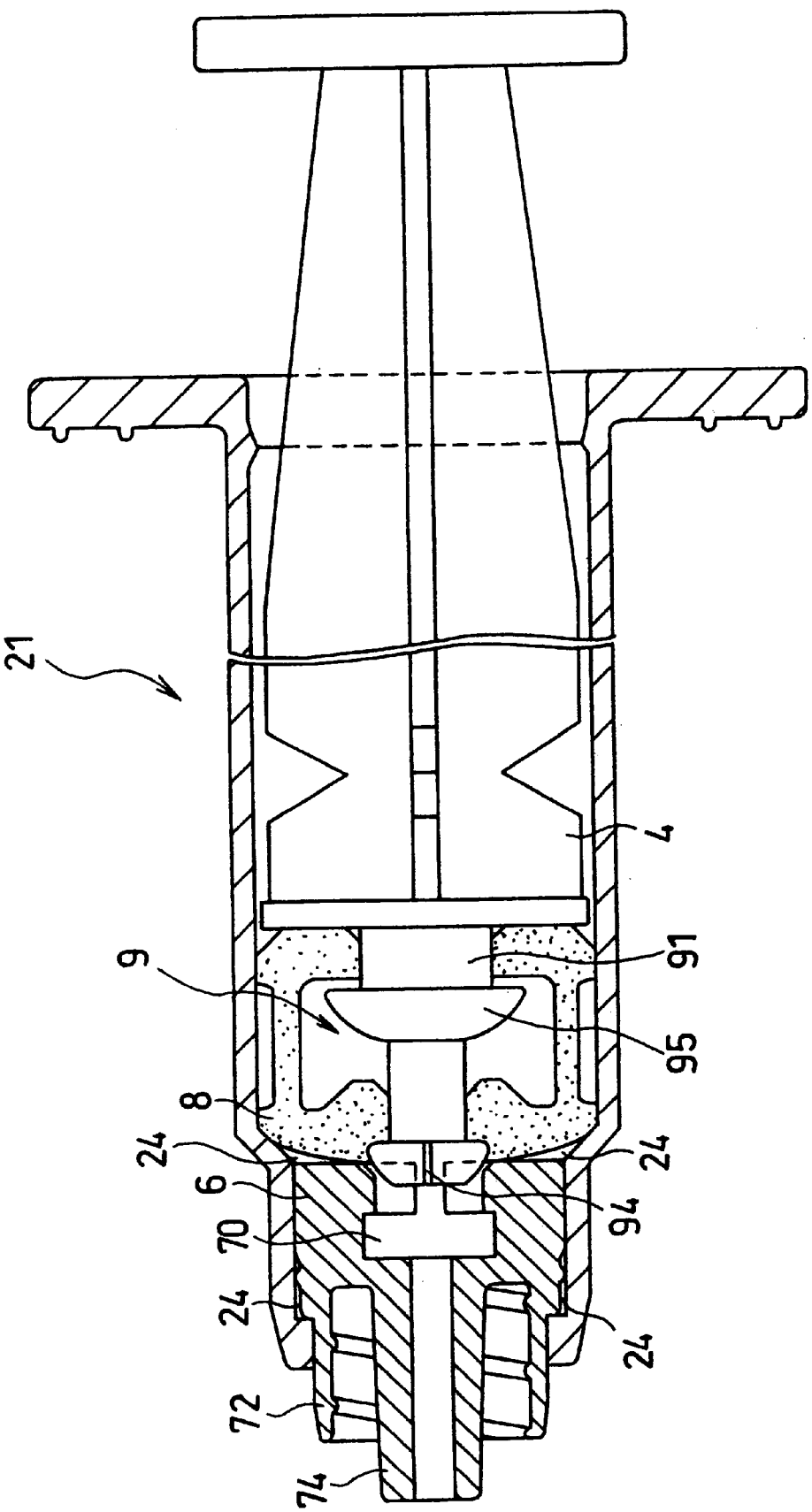
FIG. 5 is a type sectional view, showing an engaging state of the needle support and the piston.

A disposal procedure of the syringe 1 will be described with reference to FIGS. 2 and 5 to FIG. 7. Shown in FIG. 5 is a state of the injection having practically completed. Here, the piston 4 is further pressed in the direction of the needle support 6 and the locking projection 9 is engaged with the locking hole 70 of the needle support 6 as shown in FIG. 2. At this time, parenteral solution, the air and the like left inside the body's space 28 formed in the inside of the syringe body 21 as shown in FIG. 5 are led into the pass-through hole 63 and discharged outside through the syringe needle 7.

On the other hand, slipping off of the needle support 6 in the pressing direction when the locking projection 9 is engaged with the locking hole 70 is prevented by the action of the stage portion 62 of the needle support 6 and the stopper 32 of the tip of the smaller-diameter portion 23. The taper face 97 of the insertion portion 93 in the tapered shape is attachably guided to the taper face 66 of the introductory portion 65 and advances toward the holder portion 68, while expanding (deforming) the inner peripheral face of the necking portion 69. At this time, the slit 76 is widened to help this expansion (deformation). The insertion portion 93 reaching the holder portion 68 expands the inner peripheral face of the holder portion 68 in the radial direction. At the same time, the pillar option 91 expands the inner peripheral face of the necking portion 69 in the radial direction. A series of these expanding actions generate the compressive stress acting in various directions inside the needle support 6 and this compressive stress acts upon the smaller-diameter portion 23.

Each arrow shown inside of the needle support 6 of FIG. 4 artificially represents this compressive stress. One part of the compressive stress expands the smaller-diameter portion 23 in the radial direction through a press face 67, thereby disengaging (slightly disengaging) the engagement of the annular projection 31 and the annular protrusion 61 (the locking structure 100). On the other hand, since one part of the expanded needle support 6 is absorbed by the clearance space 24, no effect is exerted on the smaller-diameter portion 23. This is the reason why the clearance space 24 was formed between it and the smaller-diameter portion 23 by partially making the needle support 6 narrower. This is because, if any effect is exerted, the annular protrusion 61 is also expanded in the radial direction and, as a result, its engagement with the annular projection 31 can not be disengaged. At the same the engagement of the annular projection 31 and the annular protrusion 61 is disengaged, reaction from the compressive stress received from the stopper 32 pushes back the needle support 6 in the drawing out direction. Since this pushing back force helps a drawing out force required when the piston is drawn out, smooth drawing-out is realized by a small force.

Even in the case where the engagement is not disengaged but only slightly disengaged, when the piston 4 is drawn out and the engagement is forcibly disengaged, a reaction from the stopper 32 helps a pull-out and a smooth pull-out is realized without a big force. In this case, a circular arc face 33 of the annular protrusion 61 always makes the touch area with the annular projection 31 small and makes climbing over the annular projection 31 smooth. Further, the circular arc face 33 which climbed over the annular projection 31 abuts on the inclined face 64 (reference to FIG. 3) and even a partial output in the drawing-out direction is acted. By making climbing over the annular projection 31 smooth and the partial output in the drawing-out direction acted, the piston 4 can be drawn out with a small force by that much.

Figure 6:
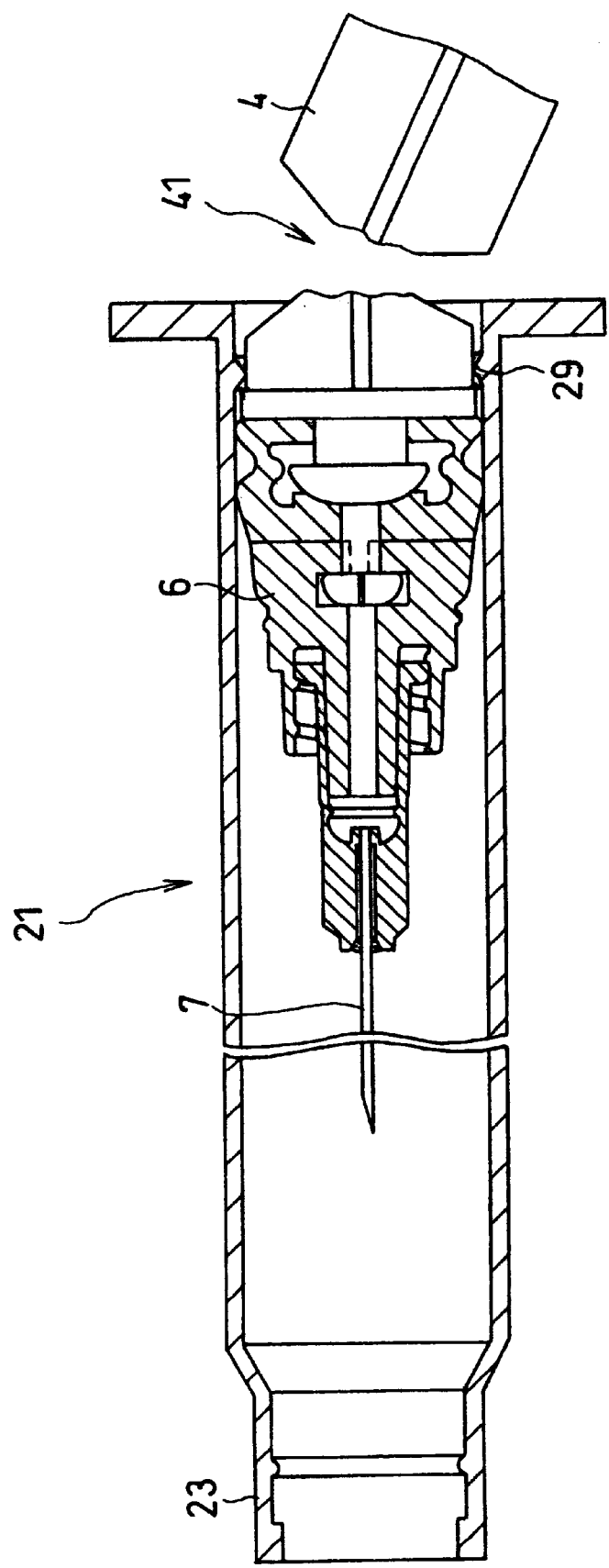
FIG. 6 is a view of the piston being broken off.

Here, when the piston 4 is further drawn out in the drawing out direction, a state thereof stands as shown in FIG. 6. Shown in FIG. 6 is a state of the needle support 6 with the syringe needle 7 being pulled into the inside of the syringe 21 and stored there. When the syringe needle 7 is kept in a state of being stored, even if it is disposed as it is, since many and unspecified persons will not be directly touched by the syringe needle 7, there is no fear that a secondary infection is triggered owing to blood and the like attached to the syringe needle 7. A role for preventing the needle support 6 (the syringe needle 7) from slipping out of the syringe body 21 again owing to excessive drawing-out is borne by a stop rib 29. As shown by FIG. 6, after the piston 4 is abutted on the stop rib, the piston 4 is broken off from the notch 41 part and disposed. By this manner, the disposed syringe 1 can be made not bulky.

Figure 7:
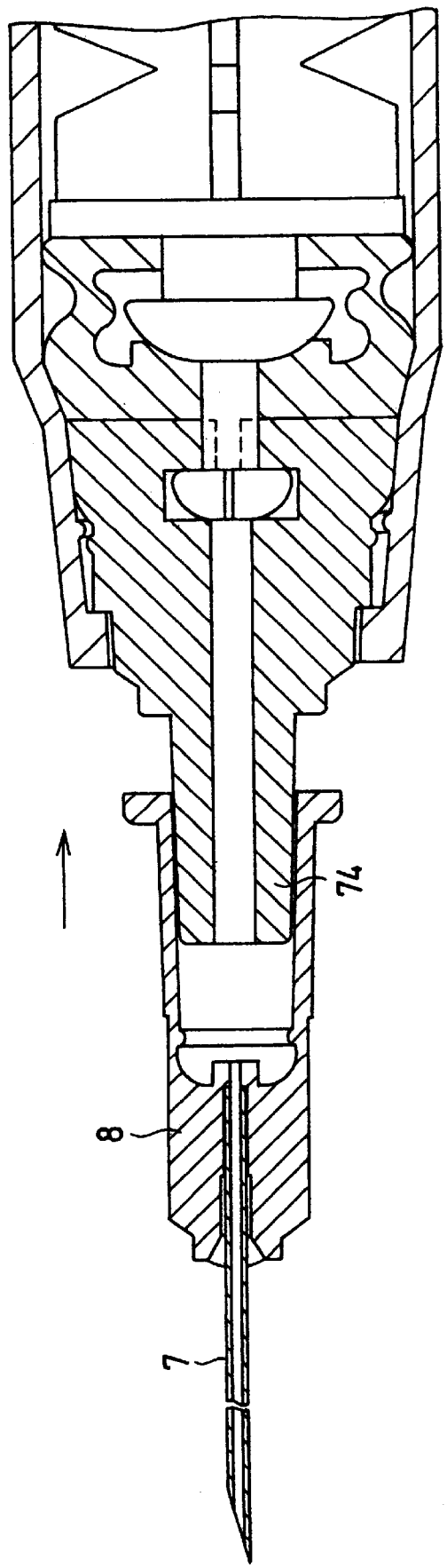
FIGS. 7 and 8 are diagrams, showing modified examples of the present embodiment.
Figure 8:
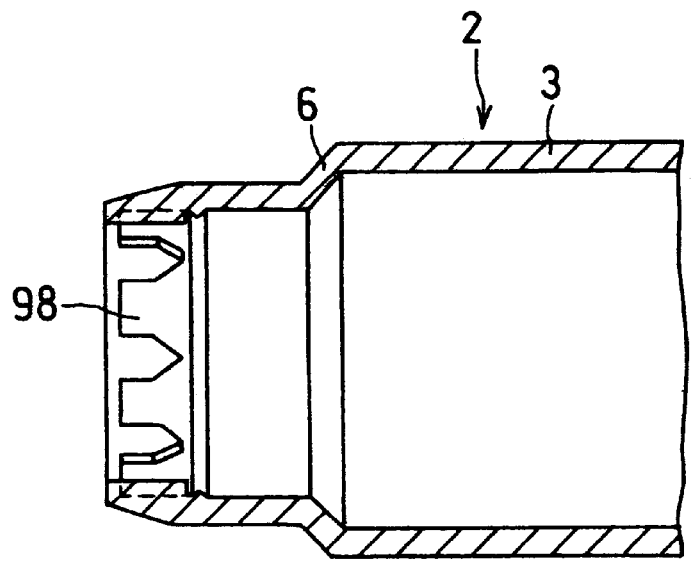
Figure 9:
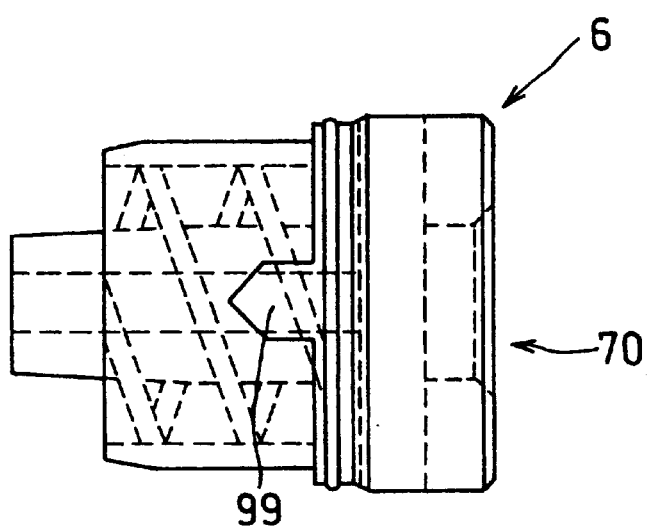
FIG. 9 is a side view of a needle support corresponding to the syringe of FIG. 8.

Shown in FIG. 7 is a modified example of the present embodiment (hereinafter referred to as "the present modified example"). Difference between the present modified example and the present embodiment is that the present modified example does not have a screw portion by which the hub 8 is installed. Installment of the syringe needle in the present modified example is designed to be executed by fitting the hub 8 into the insertion portion 74. The screw portion 72 is for preventing the fitted hub 8 from slipping off. Further, as shown in FIG. 8, concave portions 98, 98 are formed in a tip inner wall of the smaller-diameter portion 23, into which convex portions 99 (FIG. 9) formed in the needle support 6 are fitted so that the needle support 6 may be designed not to turn in the circumferential direction against the smaller-diameter portion 23.

INDUSTRIAL AVAILABLE POSSIBILTY

As described above, the syringe according to the present invention is suitable mainly for medical treatment as a disposable syringe.

What is claimed is:

1. A syringe comprising:

a syringe body, a piston sliderably inserted from one end of said syringe body, a smaller-diameter portion formed in the other end of said syringe body, a needle support detachably supported by said smaller-diameter portion, a syringe needle supported by said needle support, a path-through hole formed in said needle support for communicating with a flow passage of said syringe needle and an inside of said syringe body, a stopper formed on a tip portion of said smaller-diameter portion for preventing said needle support from slipping off in the other end direction of said syringe body, a locking projection projecting from a tip an the axis center direction of said piston, and a locking hole disposed on a side of said position of said needle support for engaging with said locking projection when said piston is pressed in;

wherein, in said syringe constituted such that said syringe needle, after said locking projection is inserted into said locking hole by pressing in said piston, is drawn into the inside of said syringe body together said needle support and stored there by pulling out said piston, a locking piston structure for preventing said needle support form slipping off in one end direction of said syringe body is provided between an inner peripheral face of said smaller-diameter portion and an outer peripheral face of said needle support, and a seal structure for preventing liquid leak in the engaging portion of said locking structure is formed, and when said locking projection is inserted into and engaged with said locking hole, said locking projection and said locking hole are formed in such a shape that said needle support is deformed and the inner peripheral face of said smaller-diameter portion is expanded in the radial direction so as to be able to disengage the engagement of said locking structure.

2. The syringe as claimed in claim 1, wherein an outer diameter of said locking projection before the engagement is larger than an inner diameter of said locking hole before the engagement.

3. The syringe as claimed in claim 1, wherein a slit for deformation promotion formed along with said locking hole in a longitudinal direction of said needle support is formed on said needle support.

4. The syringe as claimed in claim 3, wherein sad locking projection comprises a communication path for communicating with the inside of said syringe body and said pass-through hole when engaged with said locking hole.

5. The syringe as claimed in claim 1, wherein said locking structure is formed such that a compressive force in a direction of said stopper is acted on said needle support supported by said smaller-diameter portion, and said needle support is formed so as to be elastically deformed by said compressive force.

6. The syringe as claimed in claim 5, wherein said locking structure comprises an annular projection projecting toward its center from the inner peripheral face of said smaller-diameter portion and an annular protrusion protruding in a radial direction from the outer peripheral face of said needle support, and said annular protrusion is located at the other side of said syringe body from said annular projection.

7. The syringe as claimed in claim 6, wherein said annular projection comprises an inclined face inclining downward to one end direction of said syringe body.

8. The syringe as claimed in claim 6, wherein said annular protrusion is formed so as to bite into said smaller-diameter portion when engaged with said annular projection.

9. The syringe as claimed in claim 8, wherein either one of said smaller-diameter portion and said needle support is formed of materials softer than the other one.

10. The syringe as claimed in claim 9, wherein said annular projection is circular arc in its sectional shape of the diameter direction.

11. The syringe as claimed in claim 2, wherein a slit for deformation promotion formed along with said locking hole in a longitudinal direction of said needle support is formed on said needle support.

12. The syringe as claimed in claim 2, wherein said locking structure is formed such that a compressive force in a direction of said stopper is acted on said needle support supported by said smaller-diameter portion, and said needle support is formed so as to be elastically deformed by said compressive force.

13. The syringe as claimed in claim 4, wherein said locking structure is formed such that a compressive force in a direction of said stopper is acted on said needle support supported by said smaller-diameter portion, and said needle support is formed so as to be elastically deformed by said compressive force.

14. The syringe as claimed in claim 7, wherein said annular protrusion is formed so as to bite into said smaller-diameter portion when engaged with said annular projection.

* * * * *

UNITED STATES PATENT AND TRADEMARK OFFICE
CERTIFICATE OF CORRECTION

PATENT NO. : 6,196,997 B1
DATED : March 6, 2001
INVENTOR(S) : Yoshikuni Saito

It is certified that error appears in the above-identified patent and that said Letters Patent is hereby corrected as shown below:

Column 1,
Line 39, "the" should read -- The --.

Column 2,
Line 4, insert -- point -- after "view".

Column 5,
Lines 18, 22, 28, 33 and 40, "diamter" should read -- diameter --.

Column 6,
Line 1, "section" should read -- sectional --.
Lines 33, 34, and 52, "diamter" should read -- diameter --.
Line 51, "projecting" should read -- projection --.

Column 7,
Line 30, "ad" should read -- and --.
Line 58, after "syringe" insert -- body --.

Column 8,
Lines 53 and 54 "communication" should read -- communicating --.
Line 61, "taperng" should read -- tapering --.

Column 11,
Line 6, remove the word "piston".

Signed and Sealed this

Twentieth Day of August, 2002

*Attest:*

JAMES E. ROGAN
*Attesting Officer*    *Director of the United States Patent and Trademark Office*